United States Patent
Bernard et al.

(10) Patent No.: US 9,658,212 B2
(45) Date of Patent: May 23, 2017

(54) PROCESS FOR EVALUATING ACTIVE AGENT(S) CAPABLE OF PRESERVING THE FUNCTIONALITY OF EPITHELIAL STEM CELLS

(71) Applicant: L'OREAL, Paris (FR)

(72) Inventors: Bruno Bernard, Courbevoie (FR); Michelle Rathman Josserand, La Celle St Cloud (FR)

(73) Assignee: L'Oreal, Paris (FR)

(*) Notice: Subject to any disclaimer, the term of this patent is extended or adjusted under 35 U.S.C. 154(b) by 187 days.

(21) Appl. No.: 14/378,415

(22) PCT Filed: Feb. 7, 2013

(86) PCT No.: PCT/EP2013/052375
§ 371 (c)(1),
(2) Date: Aug. 13, 2014

(87) PCT Pub. No.: WO2013/117618
PCT Pub. Date: Aug. 15, 2013

(65) Prior Publication Data
US 2016/0018388 A1    Jan. 21, 2016

Related U.S. Application Data

(60) Provisional application No. 61/600,218, filed on Feb. 17, 2012.

(30) Foreign Application Priority Data

Feb. 7, 2012   (FR) ...................................... 12 51120

(51) Int. Cl.
*G01N 33/50* (2006.01)
*C12Q 1/68* (2006.01)

(52) U.S. Cl.
CPC ....... *G01N 33/5073* (2013.01); *C12Q 1/6883* (2013.01); *G01N 33/5023* (2013.01); *C12Q 2600/136* (2013.01); *C12Q 2600/158* (2013.01); *G01N 2333/4703* (2013.01); *G01N 2333/988* (2013.01); *G01N 2800/20* (2013.01); *G01N 2800/7038* (2013.01)

(58) Field of Classification Search
None
See application file for complete search history.

(56) References Cited

U.S. PATENT DOCUMENTS

| 2006/0084123 A1* | 4/2006 | Harris .................. C12Q 1/527 435/7.23 |
| 2016/0030365 A1* | 2/2016 | Giuliani .................. A61K 8/41 424/93.7 |

OTHER PUBLICATIONS

Garza L. et al. Bald Scalp in Men with Androgenetic Alopecia Retains Hair Follicle Stem Cells but Lacks CD200 Rich and CD34 Positive Hair Follicle Progenitor Cells. J of Clinical Investigation 121(2)613-622, Feb. 2011.*
Kaluz S. et al. Transcriptional Control of the Tumor and Hypoxia Marker Carbonic Anhydrase 9. Biochimica et Biophysica Acta 1795(2)162-172, 2009.*
Weir L. et al. Effects of Hypoxia Upon Differentiation and Proliferation of Epidermal Keratinocytes. J of Investigative Dermatology 130(Suppl 1) S72 #430, 2010.*
Park B. et al. Hair Growth Stimulated by Conditioned Medium of Adipose Derived Stem Cells is Enhanced by Hypoxia. Biomedical Research 31(1)27-34, Feb. 2010.*

* cited by examiner

*Primary Examiner* — Ralph Gitomer
(74) *Attorney, Agent, or Firm* — Polsinelli PC

(57) ABSTRACT

The present invention relates to a process for evaluating in vitro at least one active agent capable of preserving the functionality of epithelial stem cells, in particular of maintaining or stimulating the growth and/or the density and/or the renewal of a keratin material, consisting in determining the ability of the active agent(s) to mimic a hypoxic state in the keratin material, the active agent(s) being capable of increasing the expression of at least carbonic anhydrase IX as biological marker of hypoxia, in the keratin material treated with the active agent(s) compared with the keratin material not treated with the active agent(s). It also relates to the use of such a process.

20 Claims, 1 Drawing Sheet

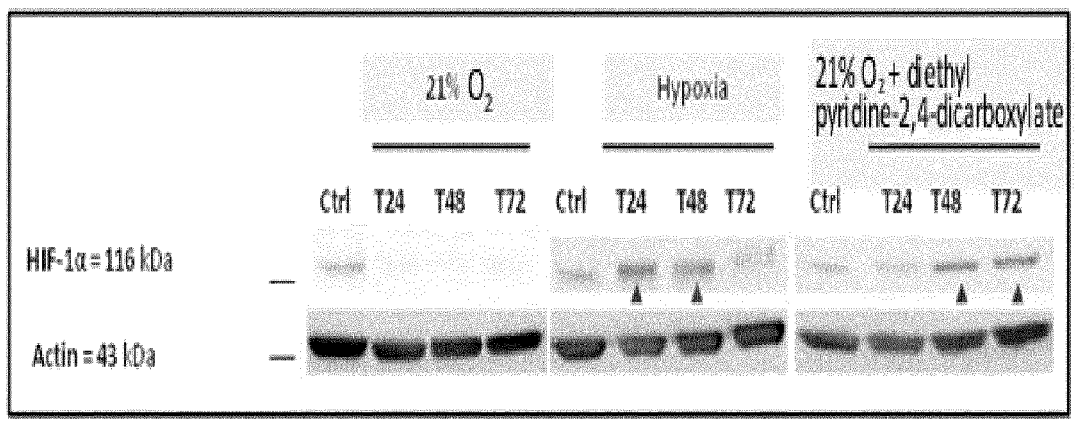

PROCESS FOR EVALUATING ACTIVE AGENT(S) CAPABLE OF PRESERVING THE FUNCTIONALITY OF EPITHELIAL STEM CELLS

CROSS REFERENCE TO RELATED APPLICATIONS

This application is a National Phase filing under 35 U.S.C. §371 of PCT/EP2013/052375 filed on Feb. 7, 2013; and this application claims priority to Application No. 1251120 filed in France on Feb. 7, 2012; and this application claims the benefit of U.S. Provisional Application No. 61/600,218 filed on Feb. 17, 2012. The entire contents of each application are hereby incorporated by reference.

The present invention relates to a process for evaluating in vitro at least one active agent capable of preserving the functionality of epithelial stem cells, in particular of maintaining or stimulating the growth and/or the density and/or the renewal of a keratin material, in particular of the hair or of the skin. In particular, such an evaluation process is of use for selecting candidates that act to maintain or increase hair density and/or to combat aging of the skin

BACKGROUND OF DISCLOSURE

Keratin materials, and in particular the head of hair and the skin, comprise epithelial stem cells which, generally, in addition to their pluripotent capacity, are capable of differentiating into various cells which make up the tissues of the body and of self-renewing. These functionalities are necessary for regenerating the tissues, but can undergo certain modifications or dysfunction over time.

In particular, the human head of hair represents a collection of approximately 150 000 hairs. Each one of them is generated by a specialized secondary component of the skin, a truly autonomous organ, the hair follicle. The growth of the hair and the renewal thereof is not a continuous process, it been determined by the activity of the hair follicles and their matrix environment. The activity of such follicles is cyclic and comprises essentially four phases. Indeed, the follicle goes successively from a growth phase with production of the hair shaft (anagen phase), to a rapid involution phase (catagen phase), then to a resting phase with hair loss (telogen phase), which precedes a regeneration (neogen) phase so as to once again arrive at the anagen phase. The anagen phase, an active or growth phase during which the hair gets longer, lasts several years. The very short catagen phase lasts a few weeks. The telogen phase or resting phase lasts a few months. At the end of this resting period, the hairs fall out and another cycle recommences. The head of hair is therefore undergoing constant renewal and, out of the approximately 150 000 hairs which make up a head of hair, approximately 10% are resting and will be replaced over the coming months.

Natural hair loss can be estimated, on average, at a few hundred hairs per day for a normal physiological state. This constant physical renewal process undergoes a natural change during aging, the hairs become thinner and their cycles become shorter.

Various causes can, however, lead to considerable temporary or definitive hair loss. Hair loss, in particular alopecia, is essentially caused by disruptions of hair renewal. These disruptions lead, initially, to shortening of the anagen phase and gradual thinning of the hair, and then a decrease in the amount thereof. Gradual miniaturization of the bulbs occurs, with, in conjunction, isolation thereof through gradual thickening of the collagen matrix of the outer connective sheath. The revascularization around the hair follicle is therefore made more difficult with each cycle. The hairs regress, and miniaturize until they are no more than a non-pigmented down, and this phenomenon leads to gradual depletion of the head of hair.

Areas are preferentially affected, in particular the temporal or frontal lobes in men, and in women, diffuse alopecia of the crown of the head is observed.

The term alopecia also covers an entire family of hair follicle damage resulting in the end in partial or general definitive hair loss. This is more particularly androgenic alopecia. In a considerable number of cases, premature hair loss occurs in genetically predisposed individuals, it is then androchronogenetic alopecia; this form of alopecia concerns in particular men.

It is, moreover, known that certain factors, such as a hormonal imbalance, a physiological stress or malnutrition, can accentuate the phenomenon. In addition, hair loss or modification may be connected to seasonal phenomena.

Generally, any factor which influences these processes, namely acceleration of cycle frequency, gradual bulb miniaturization, gradual thickening of the perifollicular collagen matrix, thickening of the outer connective sheath, and a decrease in vascularization, will have an effect on hair follicle growth.

The hair follicle is structurally composed of two distinct compartments: an epithelial compartment and a dermal (mesenchymal) compartment, and the interaction of these two compartments is essential for hair morphogenesis and regrowth and also for maintaining the follicular cycle. The maintaining of the functionality of the epithelial compartment is dependent on the presence and on the activity of various stem cell reservoirs. A first reservoir of epithelial stem cells was identified in a region called the "bulge" in rodents (Cotsarelis G, Sun T T, Lavker R M. (1990) Cell 61: 1329-1337). Since this first discovery, other reservoirs of keratinocyte stem cells have been identified, always in rodents. These stem cells play an essential role in follicle morphogenesis, but they are also involved in epidermal repair in the event of injury. Studies on human follicles are much more rare, but reveal at least two reservoirs of epithelial stem cells characterized by the expression of keratin 19, which are nested in the outer root sheath (ORS) of the follicle (upper third and lower third) (Commo S, Gaillard O, Bernard B A. (2000) Differentiation 66:157-164).

Although these stem cell reservoirs are acknowledged to be absolutely essential for maintaining and regenerating the hair follicle, there is, at the current time, very little knowledge regarding the modification of these cell populations with age and/or with the beginning and the progression of alopecia (all types of alopecia included). It has recently been demonstrated that hair loss in men with alopecia is accompanied by a disappearance not of stem cells, but rather of certain populations of progenitor cells (more active, proliferative cells). These results suggest that alopecia could be linked to a problem of follicle stem cell activation or else of the expression of the complete regenerative potential of the progenitor cells (L A Garza et al. (2011) J Clin Invest. 121: 613-622).

The identification of technical solutions which allow better preservation of the functionality/activity of follicular epithelial stem cells would therefore be very important with a view to preserving hair quality, density and shape throughout an individual's life.

Given the importance of the microenvironment (niche) in the regulation of the activity and of the functionality of stem cells in diverse and varied tissues, the inventors have undertaken studies in order to identify environmental factors which could regulate the activity of epithelial stem cells.

To do this, in addition to investigations on follicular epithelial stem cells, the inventors have at the same time broadened their investigation to skin epithelial cells.

SUMMARY OF DISCLOSURE

Surprisingly and unexpectedly, the inventors have thus discovered that certain reservoirs of follicular or skin epithelial stem cells bathe in a hypoxic environment. This observation was revealed through carbonic anhydrase IX, a protein of which the expression increases under hypoxic conditions (S Kaluz et al. (2010) Biochim Biophys Acta 1795:162-172).

By demonstrating, by means of double immunofluorescent detection tests, that a subset of carbonic anhydrase IX expresses CD34, and taking this in combination with the publication L A Garza et al. (2011) J Clin Invest. 121: 613-622 showing that stem cells bearing CD34 are depleted in individuals with alopecia, the inventors have therefore formulated the hypothesis that the induction of a signal of a hypoxic state is capable of maintaining the functionality of epithelial stem cells.

A subject of the present invention is therefore a process for evaluating in vitro at least one active agent capable of preserving the functionality of epithelial stem cells, in particular of maintaining or stimulating the growth and/or the density and/or the renewal of a keratin material, consisting in determining the ability of the active agent(s) to mimic a hypoxic state in the keratin material, preferentially under normoxic conditions, the active agent(s) being capable of increasing the expression of at least carbonic anhydrase IX as biological marker of hypoxia, in the keratin material treated with the active agent(s) compared with a keratin material not treated with the active agent(s), preferentially under normoxic conditions.

BEST AND VARIOUS MODES FOR CARRYING OUT DISCLOSURE

Preferentially, this process consists in determining the ability of the active agent(s) to mimic a hypoxic state in the keratin material, following treatment of the keratin material in a normoxic state with the active agent(s).

The term "mimic" is intended to mean that the active agent(s) is (are) capable of increasing the expression of (i.e. expressing or overexpressing) a biological marker of hypoxia, in this case at least carbonic anhydrase IX, which is normally barely or not at all expressed in the normoxic state.

The term "normoxic state" is intended to mean a level of dioxygen corresponding to that of the ambient terrestrial atmosphere, i.e. 21%.

The term "hypoxic state" is intended to mean a level of dioxygen that is strictly less than that of the ambient terrestrial atmosphere, for example less than 5%, for example equal to 3%.

Thus, the active agent(s) has (have) the ability, starting from a keratin material in the normoxic state, to move said keratin material to a state of hypoxic type, thus being able to cause effects comparable to those of a hypoxic microenvironment for the epithelial stem cells.

The expression of at least carbonic anhydrase IX as biological marker of hypoxia can be demonstrated by labeling carbonic anhydrase IX in its protein form, preferably by immunofluorescent labeling or Western blotting of said protein, and/or by transcriptomic analysis of carbonic anhydrase IX.

A dependent or independent objective of the process as previously defined may consist, as a variant or additionally, in observing the expression of one (or more) biological marker(s) of hypoxia, such as carbonic anhydrase IX, in the basal layer of the proximal region of the outer sheath of a hair follicle.

To the inventors' knowledge, no prior art document either teaches or suggests using such a process for evaluating active agent(s) with regard to their ability to mimic hypoxia, in particular by analyzing the expression of at least carbonic anhydrase IX as biological marker of this hypoxia, in particular with a view to studying their property of preserving the functionality of epithelial stem cells, the previous studies having for the moment essentially shown that hypoxic conditions have a considerable impact on the biology of embryonic stem cells (U Silvan et al (2009) Differentiation 78:159-168) and also the biology of stem cells derived from adult tissues, such as neuronal stem cells or hematopoietic stem cells (P Eliasson et J I Jonsson (2010) J Cell Physiol 222:17-22; D M Panchision (2009) J Cell Physiol 220:562-568).

At the cellular level, the hypoxic conditions have an impact in particular on the control of the cell cycle, the metabolism and the ability to respond to oxidative stress. The cellular response to hypoxic conditions is under the control of HIFs (hypoxia-inducible factors), and in particular HIF-1 which is a transcription factor composed of 2 subunits, HIF1-α (alpha) and HIF1-β (beta), and which regulates the transcription of more than 100 genes involved in the cell cycle, viability, differentiation, autophagy, etc. The activation of HIF1 is finely regulated according to the oxygenation state of the cells. Under conditions of high oxygenation ("normoxia"), the HIF1-alpha subunit is hydroxylated by prolyl 4-hydroxylase, which enables its ubiquination and its degradation by the proteasome. Conversely, when the dioxygen pressure decreases (hypoxia), this subunit is no longer degraded and can then accumulate and migrate to the nucleus so as to bind to the HIF1-beta subunit and thus form the transcription factor HIF1.

A preferential solution in the context of this evaluation process may thus consist in determining whether the active agent(s) to be tested, corresponding to the evaluation process according to the invention, have the ability to act as inhibitors of prolyl hydroxylase with a view to preventing its degradation of this transcription factor, and in particular the α (alpha) subunit of the HIF-1 protein, and thus maintaining a hypoxic state of the epithelial stem cells. Of course, this route of action should not be considered to be limiting, it being possible for the active agent(s) to be involved in one or more other additional or different route(s) of action with a view to producing this hypoxic effect.

A subject of the present invention is also the use of an evaluation process as previously defined in order to determine one (or more) active agent(s) capable of maintaining or increasing hair density and/or capable of combating skin aging.

Other characteristics, properties and advantages of the present invention will emerge more clearly on reading the description and the examples that follow.

Keratin Materials

The evaluation process according to the present invention uses keratin materials.

The term "keratin materials" is intended to mean keratin fibers and the skin. Keratin fibers concern in particular the hair, the eyebrows, the eyelashes and bodily hair. Preferentially, keratin fibers refer to the hair.

Such a keratin material is tested in vitro in the sense that it is tested in isolation from the organism to which it belongs.

To do this, it may, for example, be derived from surgical waste, from a biopsy, from a culture of follicular or skin keratinocytes or from a culture of epithelial stem cells, for example a follicular or skin epithelial stem cell culture.

Active Agents

The evaluation process according to the present invention uses at least one active agent to be brought into the presence of the isolated keratin material as previously defined.

Preferably, the active agent(s) to be tested on the keratin material is (are) capable of mimicking hypoxia on a keratin material tested under normoxic conditions.

An active agent in accordance with the present invention is tested with regard to its ability to increase the expression of (i.e. to express or overexpress) at least carbonic anhydrase 9, as biological marker of hypoxia, within said isolated keratin material.

Such an active agent may also be tested with regard to its ability to express or overexpress one or more other biological marker(s) of hypoxia.

For example, according to one particular embodiment, this active agent may be tested with regard to its ability to increase the expression of (i.e. express or overexpress) glucose transporter 1 (GLUT-1), as biological marker(s) of hypoxia.

According to one particular embodiment, this active agent acts indirectly on the HIF-1 protein. In particular, this active agent acts on an HIF-1 degradation enzyme. More specifically, this active agent preferentially acts as a prolyl hydroxylase inhibitor.

Preferentially, the active agent(s) is (are) capable of acting, independently of the level of cellular oxygenation, on the stabilization of the level of expression of the HIF-1 protein.

Also preferably, this active agent does not result in a transcriptomic variation of HIF-1, in particular does not result in a variation of HIF-1 gene expression.

Consequently, said active agent acts preferentially, only, and indirectly, on the HIF-1 protein.

Evaluation Process

The evaluation process according to the invention aims to study the effects of one or more active agent(s) on the preservation of the functionalities of epithelial stem cells by observing their ability to mimic a hypoxic state on an isolated keratin material, by observing the expression of at least carbonic anhydrase IX as biological marker of hypoxia, compared with an untreated control keratin material.

A first evaluation process may consist in carrying out a labeling, preferably immunolabeling, for example by immunofluorescence or Western blotting, of at least the carbonic anhydrase IX protein as biological marker of hypoxia. More particularly, analyses of keratin materials, such as of tissues derived from human scalp, in particular hair follicles, or of follicular or skin keratinocyte cultures, with antibodies specific for carbonic anhydrase IX, a biological marker of hypoxia, can be used in order to observe variations in expression, respectively under hypoxic conditions and under normoxic conditions in the presence or absence of active agent(s) in order to study whether the active agent(s) is (are) capable of mimicking a hypoxic state.

A second evaluation process may consist in carrying out a transcriptomic analysis of carbonic anhydrase IX, of which the expression of the corresponding gene is modified by a hypoxic signal, using the RT-qPCR technique, on keratin materials, for example on in vitro cultures of keratinocytes or hair bulbs isolated by microdissection and placed in culture ex vivo, under hypoxic conditions, and under normoxic conditions in the presence or absence of said active agent(s) to be tested, in order to study whether the active agent(s) is (are) capable of mimicking a hypoxic state.

It is possible to optionally add to these two evaluation processes a process aimed at establishing the impact of the active agent(s) capable of mimicking hypoxia on the quality of the epithelial stem cells. To do this, a CFE (Colony-forming efficiency) test can be carried out for keratinocytes (including epithelial stem cells), consisting in observing, respectively, under hypoxic conditions and under normoxic conditions in the presence or absence of active agent(s), the impact of the presence of the active agent(s) on the frequency of the cells capable of generating a cell clone within a given population, and also on the clonal morphology obtained, so as to thus establish their participation in the preservation of the functionality of the epithelial stem cells treated with the active agent(s).

According to one illustrative and nonlimiting embodiment, at least one of these evaluation processes or all of these evaluation processes can be implemented in order to establish the effect of one or more active agent(s) on the expression of at least carbonic anhydrase as biological marker of hypoxia.

KEY TO THE FIGURE

FIG. 1: Analysis of the level of expression/stabilization of the HIF1-alpha protein by Western blotting.

EXAMPLES

Several examples of evaluation processes according to the invention have been given below by way of illustration of the present invention. Such examples do not limit the scope of the invention, those skilled in the art being able to use other processes known per se in order to demonstrate the stimulation of carbonic anhydrase IX as biological marker of hypoxia on keratin materials.

I—Protocol and Results

By way of illustration of active agents corresponding to the evaluation process according to the invention, mention may be made of pyridinedicarboxylic acids and certain derivatives, in particular esters and amides. By way of example, a compound known to be suitable for inhibiting prolyl hydroxylase was used, in this case a compound chosen from derivatives of pyridinedicarboxylic acid of general formula (I) or one of their salts:

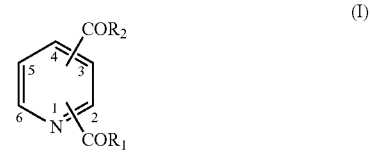

in which formula (I):

R$_1$ and R$_2$ represent, independently of one another, OH, OR', —NH$_2$, —NHR' or —NR'R", with R' and R" representing, independently of one another, a saturated or unsaturated, linear or branched C$_1$-C$_{18}$ alkyl radical, or an aryl radical, this aryl or alkyl radical being optionally substituted with at least one OH, alkoxy, acyloxy, amino ou alkylamino group, or R' and R" together represent a heterocycle, as mentioned in application EP1352629, and in particular diethyl pyridine-2,4-dicarboxylate was used.

1/ First Evaluation Process Example

This first process consisted in observing, with an optical fluorescence microscope, a hair follicle after immunofluorescent labeling using antibodies specific for carbonic anhydrase IX, a biological marker of hypoxia, in the absence and presence of diethyl pyridine-2,4-dicarboxylate.

By virtue of this process, it is possible to observe expression of the carbonic anhydrase IX protein, which what is more is located in the basal layer of the proximal region of the outer sheath of the hair follicle containing the follicular epithelial stem cells.

2/ Second Evaluation Process Example

This second process consists in carrying out a transcriptomic analysis of the gene encoding carbonic anhydrase IX, the expression of which is modified by a hypoxic signal, using the RT-qPCR technique, on hair bulbs isolated by microdissection at the level of the human scalp hypodermis and placed in culture ex vivo for 4 hours either under hypoxic conditions (3% dioxygen) or at 21% dioxygen, in the absence (control) or in the presence of diethyl pyridine-2,4 dicarboxylate.

After 4 hours of incubation of the whole bulbs under hypoxic conditions or under normoxic conditions in the presence of diethyl pyridine-2,4-dicarboxylate, standard expression of carbonic anhydrase 9 is observed, indicating that the treatment with diethyl pyridine-2,4-dicarboxylate induces a molecular profile similar to that induced by hypoxia.

3/ Third Evaluation Process Example

This third example consists in carrying out an analysis of the level of expression/stabilization of the HIF1-alpha protein using the Western blotting technique as a basis. To summarise, under normoxic conditions, the HIF1-alpha protein is hydroxylated on a proline residue (reaction catalyzed by a prolyl hydroxylase), ubiquitinylated and then degraded by the proteasome. Under hypoxic conditions, the HIF1-alpha protein is not hydroxylated and its expression level is maintained. To characterize the effect of diethyl pyridine-2,4-dicarboxylate on the level of expression/stabilization of HIF1-alpha, a protein extract was prepared on cultures of keratinocytes derived from the outer sheath of human hair follicles maintained and placed in culture under hypoxic conditions or under normoxic conditions, in the absence or presence of diethyl pyridine-2,4-dicarboxylate. The immunodetection of the HIF1-alpha protein reveals that the expression level of this protein increases when the cells are grown in culture under hypoxic conditions (3% oxygen) compared with normoxic conditions (21% oxygen). Likewise, culturing under normoxic conditions in the presence of diethyl pyridine-2,4-dicarboxylate induces an increase in the amount of protein detected. In this regard, it may be stated that the effect of diethyl pyridine-2,4-dicarboxylate under normoxic conditions mimics the effect of hypoxic conditions on the expression/stabilization of the HIF1-alpha protein.

II—Evaluation of the Preservation of the Functionality of Epithelial Stem Cells

This evaluation of the quality of epithelial stem cells treated or not treated with the active agent(s) can, for example, be established by means of a CFE (Colony-forming efficiency) test for keratinocytes (including epithelial stem cells), consisting in observing, respectively, under hypoxic conditions and in the absence or presence of diethyl pyridine-2,4-dicarboxylate, the impact of this active agent on the frequency of cells capable of generating a cell clone within a given population and also on the clonal morphology obtained.

To do this, whole hair follicles isolated from the scalp by cosmetic surgery were cut up into pieces of 1 cm$^2$ and then treated with 2.4 U/ml diluted in a William E medium and incubated overnight at 4° C. The following day, the samples are rinsed with PBS, the epidermis is removed using tweezers, and each hair follicle is extracted and placed in PBS, on ice. After having removed the PBS, the follicles are placed in 0.5 ml of 1× trypsin-EDTA for 5 minutes at 37° C. in order to only dissociate the keratinocytes from the lower region of the outer sheath of the hair follicle. The enzymatic process is stopped by adding 1 ml of medium containing 10% of serum, and the supernatant containing the dissociated cells is then filtered using a cell screen (70 µm). The cells recovered are then centrifuged at 1000 revolutions/minute for 15 minutes at 4° C. and the cell precipitate is resuspended in a DMEM (Cambrex)—Hams F12 medium (3:1 mixture) containing 2 mM of L-glutamine and 1 mM of sodium pyruvate, supplemented with fetal calf serum 10 (HyClone), non-essential amino acids, 5 µg/ml of insulin, 0.18 mM of adenine, 0.4 µg/ml of hydrocortisone, 2 nM of triiodothyronine, 10 ng/ml of epidermal growth factor, 1 µM of isoprotenerol, 5 µg/ml of transferrin, 4 mM of glutamine and 50 U/ml of penicillin/streptomycin.

Next, the cells of the outer epithelial sheath thus extracted from the hair follicles and dissected are subsequently seeded in a proportion of 1000 cells/culture dish under CFE conditions, on a layer of irradiated 3T3 fibroblasts. The cells are then cultured either at 3% dioxygen (hypoxic conditions) or at 21% dioxygen in the presence of diethyl pyridine-2,4-dicarboxylate (in concentrations ranging from 50 to 500 µM). A control which is untreated and cultured at 21% dioxygen serves as a reference. The medium is changed on the 3rd day and on the 8th day and the culture is stopped on the 10th day. At the end of the clonogenic culture and after fixing (via 70% ethanol) and staining (incubation with eosin, rinsing and then incubation with BlueRAL 555) of the cell clones obtained, the morphology of the clones and of the cells making up these clones is analyzed.

The culturing of these cells under hypoxic conditions (3% dioxygen) very clearly has an effect on the clonal morphology. The clones obtained exhibit a more compact and less diffuse morphology (clone edges well delimited) than those obtained under conventional culture conditions at 21% dioxygen. The clones are composed of small, highly connected and more homogeneous cells which are reminiscent of the holoclones described by Y. Barrandon et H. Green (Proc. Natl. Acad. Sci. 1987, 84:2302-2306). These results were observed in a highly reproducible manner and suggest better maintenance of the immaturity of the cells in culture.

The clones obtained following treatment with diethyl pyridine-2,4-dicarboxylate are also less diffuse and less dense than the controls incubated in the presence of 21% dioxygen. In general, the clones obtained are composed of cells of very good quality. The number of clones does not significantly decrease compared with the 21% dioxygen control conditions.

In summary, the treatment with diethyl pyridine-2,4-dicarboxylate under normoxic conditions generates clones similar to those obtained under hypoxic conditions.

III—Interpretation

The inventors were able to observe co-localization of the epithelial stem cells and of carbonic anhydrase IX, the stem cells bathing in a hypoxic environment. In particular, the expression of the biological marker of hypoxia can be observed in the basal layer of the proximal region of the outer sheath of a hair follicle, also called lower reservoir of the outer sheath of the hair follicle.

The inventors showed, surprisingly and unexpectedly, that an active agent, and more specifically a prolyl hydroxylase inhibitor, which acts, independently of the level of cellular oxygenation, on the stabilization of the level of expression of the HIF1-alpha protein, partially mimics a hypoxic effect. Indeed, the treatment under normoxic conditions of the hair follicles, under survival conditions, with such a prolyl hydroxylase-inhibiting active agent induces a transcriptomic profile similar to that induced by hypoxic conditions. Moreover, the clonogenicity of the cell populations freshly isolated from the outer sheath of human hair follicles is similarly impacted whether by treatment with such prolyl hydroxylase inhibitors or by culturing under hypoxic conditions. These studies thus demonstrate that these active agents have the ability to reproduce the effects of one of the physiological characteristics (namely hypoxia) of the niche of the lower reservoir of follicular stem cells.

Of course, the active agent(s) evaluated by means of the evaluation process(es) according to the present invention can act via one or more additional or different biological pathway or pathways so as to mimic the hypoxic effect observed.

Needless to say, those skilled in the art will take care to introduce optional modifications or additions such that the advantageous properties of the evaluation process according to the invention are not, or are not substantially, adversely affected by the envisioned addition.

Throughout the application, the wording "comprising one" or "including one" means "comprising at least one" or "including at least one", unless otherwise specified.

The invention claimed is:

1. An in vitro process for evaluating at least one active agent capable of preserving the functionality of epithelial stem cells which comprises in determining the ability of the at least one active agent to mimic a hypoxic state in a keratin material selected from the group consisting of fibers and skin, the at least one active agent being capable of increasing the expression of carbonic anhydrase IX as biological marker of hypoxia, in the keratin material treated with the at least one active agent compared with the keratin material not treated with the at least one active agent.

2. The process as claimed in claim 1, which comprises determining the ability of the at least one active agent to mimic a hypoxic state in the keratin material, following treatment of the keratin material in a normoxic state with the at least one active agent.

3. The process as claimed in claim 1, wherein the at least one active agent is capable of acting, independently of the level of cellular oxygenation, on the stabilization of the level of expression of the HIF-1 protein.

4. The process as claimed in claim 1, wherein the at least one active agent is capable of acting indirectly on the HIF-1 protein in order to prevent degradation of the α (alpha) subunit of the HIF-1 protein.

5. The process as claimed in claim 1, wherein the at least one active agent is incapable of generating a transcriptomic variation of HIF-1.

6. The process as claimed in claim 1, wherein, in addition to the expression of carbonic anhydrase IX, the at least one active agent is capable of increasing the expression of glucose transporter 1 (GLUT-1) as biological marker of hypoxia, in the keratin material treated with the at least one active agent compared with the keratin material not treated with the at least one active agent.

7. The process as claimed in claim 1, wherein the expression of at least carbonic anhydrase IX as biological marker of hypoxia is demonstrated by labeling carbonic anhydrase IX in its protein form, and/or by transcriptomic analysis of carbonic anhydrase IX.

8. The process as claimed in claim 1, which comprises observing the expression of the biological marker(s) of hypoxia in the basal layer of the proximal region of the outer sheath of a hair follicle.

9. The process as claimed in claim 1, which comprises determining whether the at least one active agent is capable of maintaining or increasing hair density and/or capable of combating skin aging.

10. The process as claimed in claim 2, wherein the at least one active agent is capable of acting, independently of the level of cellular oxygenation, on the stabilization of the level of expression of the HIF-1 protein.

11. The process as claimed in claim 2, wherein the at least one active agent is capable of acting indirectly on the HIF-1 protein in order to prevent degradation of the α (alpha) subunit of the HIF-1 protein.

12. The process as claimed in claim 1, wherein the at least one active agent is capable of inhibiting prolyl hydroxylase in order to prevent degradation of the α (alpha) subunit of the HIF-1 protein.

13. The process as claimed in claim 2, wherein the at least one active agent is incapable of generating a transcriptomic variation of HIF-1.

14. The process as claimed in claim 3, wherein the at least one active agent is incapable of generating a transcriptomic variation of HIF-1.

15. The process as claimed in claim 4, wherein the at least one active agent is incapable of generating a transcriptomic variation of HIF-1.

16. The process as claimed in claim 2, wherein, in addition to the expression of carbonic anhydrase IX, the at least one active agent is capable of increasing the expression of glucose transporter 1 (GLUT-1) as biological marker of hypoxia, in the keratin material treated with the at least one active agent compared with the keratin material not treated with the at least one active agent.

17. The process as claimed in claim 3, wherein, in addition to the expression of carbonic anhydrase IX, the at least one active agent is capable of increasing the expression of glucose transporter 1 (GLUT-1) as biological marker of hypoxia, in the keratin material treated with the at least one active agent compared with the keratin material not treated with the at least one active agent.

18. The process as claimed in claim 4, wherein, in addition to the expression of carbonic anhydrase IX, the at least one active agent is capable of increasing the expression of glucose transporter 1 (GLUT-1) as biological marker of hypoxia, in the keratin material treated with the at least one active agent compared with the keratin material not treated with the at least one active agent.

19. The process as claimed in claim 5, wherein, in addition to the expression of carbonic anhydrase IX, the at least one active agent is capable of increasing the expression of glucose transporter 1 (GLUT-1) as biological marker of hypoxia, in the keratin material treated with the at least one active agent compared with the keratin material not treated with the at least one active agent.

20. The process as claimed in claim 2, wherein the expression of at least carbonic anhydrase IX as biological marker of hypoxia is demonstrated by labeling carbonic anhydrase IX in its protein form, and/or by transcriptomic analysis of carbonic anhydrase IX.

* * * * *